United States Patent
Labounty et al.

(10) Patent No.: US 6,871,211 B2
(45) Date of Patent: Mar. 22, 2005

(54) INTRANET-BASED MEDICAL DATA DISTRIBUTION SYSTEM

(75) Inventors: Scott Labounty, Orange, CA (US); David R. Clark, Irvine, CA (US); Darryn A. Johnnie, Brea, CA (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 455 days.

(21) Appl. No.: 09/818,072

(22) Filed: Mar. 27, 2001

(65) Prior Publication Data

US 2001/0044823 A1 Nov. 22, 2001

Related U.S. Application Data

(60) Provisional application No. 60/192,510, filed on Mar. 28, 2000.

(51) Int. Cl.[7] .............................................. G06F 15/16
(52) U.S. Cl. ...................... 709/203; 709/217; 600/301
(58) Field of Search ...................... 340/870.01, 870.11, 340/10.1, 10.6, 573.1; 600/300, 481, 508, 509, 301; 128/903, 904, 905; 607/30, 32, 59, 60, 27, 52; 707/10; 709/219, 230; 604/19, 48, 503

(56) References Cited

U.S. PATENT DOCUMENTS

| | | | | |
|---|---|---|---|---|
| 6,057,758 A | * | 5/2000 | Dempsey et al. | 340/539.12 |
| 6,558,321 B1 | * | 5/2003 | Burd et al. | 600/300 |
| 6,589,170 B1 | * | 7/2003 | Flach et al. | 600/300 |

* cited by examiner

Primary Examiner—Frantz B. Jean
(74) Attorney, Agent, or Firm—Andrus, Sceales, Starke & Sawall, LLP (57) ABSTRACT

A network based medical telemetry system that uses, to the greatest extent possible, standard hardware and software components. The system allows clinicians using computers anywhere in a large hospital to view physiologic data from patients of the hospital. Each patient is fitted with a set of sensors that measure physiologic properties of the patient (e.g., EKG sensors). The sensors are connected to a transmitter that relays the physiologic data to a central server. The central server comprises a WEB server that supplies basic patient data such as the patient's name and medical history. The central server also comprises a waveform server which supplies the physiologic data, in real-time or near real-time. Workstation, used by a clinician receives the basic patient data from the Web server and the physiologic data from the waveform server, and produces a combined display. The combined display is continuously updated, showing, for example, the patient's EKG.

14 Claims, 5 Drawing Sheets

INTRANET-BASED MEDICAL DATA DISTRIBUTION SYSTEM

REFERENCE TO RELATED APPLICATION

The present application claims priority from U.S. Provisional Application No. 60/192,510, filed Mar. 28, 2000, titled "INTRANET-BASED MEDICAL DISTRIBUTION SYSTEM," the entire contents of which is hereby incorporated by reference.

BACKGROUND OF THE INVENTION

1. Field of the Invention

The present invention relates to methods for real-time or near real-time distribution of medical telemetry data over a computer network. More particularly, the present invention relates to a network architecture for facilitating the efficient and reliable exchange of information between portable wireless patient monitoring devices and computers located throughout a hospital.

2. Description of the Related Art

Medical telemetry systems that allow physiologic data from multiple, remotely-located patients to be monitored from a central location are known in the art. These systems typically comprise remote telemeters that remotely collect the physiologic data of respective patients and transmit the data over a wireless link to a monitoring station. This physiologic data may include, for example, real-time electrocardiograph (EKG) waveforms, $CO_2$ levels, blood pressure, temperature, $SO_2$ levels, respiration rates, etc. From the monitoring station, a clinician can, in real-time, visually monitor the physiologic status of many different patients. The central station may also run automated monitoring software for alerting the clinician whenever a predetermined physiologic event occurs, such as a cardiac arrhythmia condition.

The remote telemeters of medical telemetry systems are generally of two types: instrument remote telemeters and ambulatory remote telemeters. An ambulatory remote telemeter is a portable, battery-powered device which permits the patient to be monitored while the patient is ambulatory. The ambulatory telemeter attaches to the patient by a strap or other attachment device, and receives the patient's physiologic data via EKG leads (and/or other types of sensor leads) which attach to the patient's body. The physiologic data is continuously transmitted to the central monitoring station by the telemeter's radio frequency (RF) transmitter to permit real-time monitoring. Instrument remote telemeters operate in a similar manner, but receive the patient's physiologic data from a bedside monitor (or other instrument) over a hardwired line, such as an RS-232 connection. Instrument remote telemeters that transfer the physiologic data to the monitoring station over a hardwired connection are also found.

Typically, the monitoring station includes a receiver for receiving and decoding the RF transmissions from the patient transmitter, and a computer for displaying the physiologic data. In many cases, the receivers are implemented as circuit boards that plug into a standard personal computer. The resulting physiologic data is displayed on the computer screen. In these applications, the process of collecting data and updating the display is relatively simple because the receiver, computer, and display are combined in a single system. Unfortunately, this type of non-networked system does not make the patient telemetry data available throughout the hospital.

For example, a monitoring station is usually placed at a nurse's station near the patient's room. If a physician, whose office is located in a different wing of the hospital, needs to view the patient's EKG, then the physician must visit the nurse's station where the data is being displayed. Another problem with non-networked monitoring is that inadequacies in the non-networked system architecture make it impractical to monitor a large number of patients (e.g., 500 to 800 or more).

Prior attempts to use computer networks to facilitate the display of physiologic telemetry data have been cumbersome and expensive because of the real-time nature of the data and the volume of data involved. In such systems, the central station consists of a receiver connected to a computer, which operates as a proprietary network data server. The data is transmitted over a dedicated network, using proprietary hardware and software, to various workstation computers (workstations) located elsewhere in the hospital. This type of system has the advantage of providing access to patient data, but at the expense of installing a custom computer network that is dedicated solely to telemetry data. Again, use of a dedicated network was necessary because of the real-time nature of the data, the volume of data, and the critical nature of the data. Even in situations, such as private networks (Intranets), where the delays introduced by other network traffic can be controlled, the overhead associated with standard protocols, such as HTTP, is often prohibitive.

It is well known to those skilled in the art of computer operating systems and networks, that the methods for handling real-time data are markedly different from those used to handle non-real-time data. Most computer operating systems are not designed to handle real-time data well. Computer operating systems that are designed to handle real-time data are generally special purpose operating systems not intended for general use. The data from most telemetry systems, including medical telemetry systems, occurs in a continuous stream, and typically must be received continuously. The operating system cannot command the sending device to stop sending the data for any appreciable length of time owing to the time critical nature of the data. For example, in a medical telemetry system that monitors patient EKG waveforms, the clinician must be notified immediately of any emergency conditions. Thus any computer, or computer network, designed to handle medical telemetry data must be capable of processing the data without undue delay. True real-time processing may not be necessary, but the processing must be close to real-time (near-real time or quasi-real time).

Standard computer networks, meaning networks that employ readily available hardware and software components (e.g., the Internet), are also typically not designed to deliver data in real-time. Standard networks, such as the Internet, are designed to deliver data as quickly as possible, but not on any set schedule. For instance, it is well known to one skilled in the art that a user downloading a large file over the Internet will typically see the data arrive in bursts separated by varying time delays. The amount of time required for a message to travel from a sending computer to a receiving computer is known as latency time. In a packet-switching network (PSN) such as the Internet, data is usually read and forwarded by several routers before it reaches its destination. No effort is made to establish a single electrical circuit between two computing devices. Instead, the sending computer divides a message into a number of efficiently sized units called packets. Each packet contains the address of the destination computer. These packets are then broadcast to the network. The packets are received by devices called routers that read each packet's destination address and, based on that address, forward the packets in the appropriate direction. Eventually, the packets arrive at their intended destination, although some may have actually traveled by different physical paths. The receiving computer assembles the packets, puts them in order, and delivers the received message to the appropriate application. Packet-switching networks are highly reliable and efficient, but they are not generally suited to the delivery of real-time data because the routing process results in variable latency times (known as jitter).

SUMMARY OF THE INVENTION

The present invention solves these and other problems by providing an architecture for near real-time distribution of data using standard network hardware and software components. The use of standard "off the shelf" hardware and software components provides a convenient way to leverage existing technology, resulting in lower cost and quicker design. The use of hardware and software developed for a packet switched network such as the Internet is particularly desirable. The use of software developed for the World-Wide Web (WWW) such as standard Web servers and Web browsers (e.g., Netscape, or Microsoft's Internet Explorer) is also particularly desirable.

The use of standard hardware and software components also allows the telemetry system to be easily customized by the hospital. Thus, even though the patient data may (in one embodiment) never leave the hospital, it is desirable to construct a hospital internal computer network using the same hardware and software components used to construct the global Internet.

One embodiment includes a patient monitoring system for providing patient data to one or more workstations connected to a computer network from one or more sensors a attached to a patient. The sensors are configured to measure physiologic data from the patient. The sensors provided data to a patient monitoring device that is configured to gather the physiologic data and use a communication system to communicate the physiologic data to a central data-monitoring device. One or more waveform servers are connected to the central data-monitoring device and to a computer network. One or more data servers are also connected to the computer network. The data servers are configured to supply data to the workstations using a first protocol. The waveform servers receive the physiologic information from the central data-monitoring device and supply the physiologic data to one or more workstations using a second protocol. In one embodiment, the communication system includes a wireless link between the patient monitoring device and the central data-monitoring device. In one embodiment, the first protocol is a low level network protocol. In one embodiment, the first protocol is TCP/IP. In one embodiment, the second protocol is a high level protocol. In one embodiment, the second protocol is an application-level protocol. In one embodiment, the second protocol uses the first protocol.

In one embodiment of the patient monitoring system, the second software program is configured to obtain said physiologic data from at least one of the waveform servers in data packets with varying latency periods, and the second software program is configured to display the physiologic data on a display device such that it appears to a person observing the display device that the physiologic data is being received as a stream of data with relatively uniform latency periods.

BRIEF DESCRIPTION OF THE FIGURES

These and other aspects, advantages, and novel features of the invention will become apparent upon reading the following detailed description and upon reference to the accompanying drawings, in which.

DETAILED DESCRIPTION

In the disclosure that follows, the term "Internet" will be understood to mean any computer network constructed using Internet compatible components. The disclosure describes the present invention in terms of the Internet only because the preferred embodiment uses Internet compatible components, and because the workings of such standard components are widely understood by those skilled in the art. One skilled in the art will appreciate that the present invention is not limited to the Internet, or Internet-compatible components. One skilled in the art will further appreciate that, even though the present invention is particularly advantageous for packet switched networks such as the Internet (or an intranet), the present invention provides benefits to any computer network.

Figure 1:
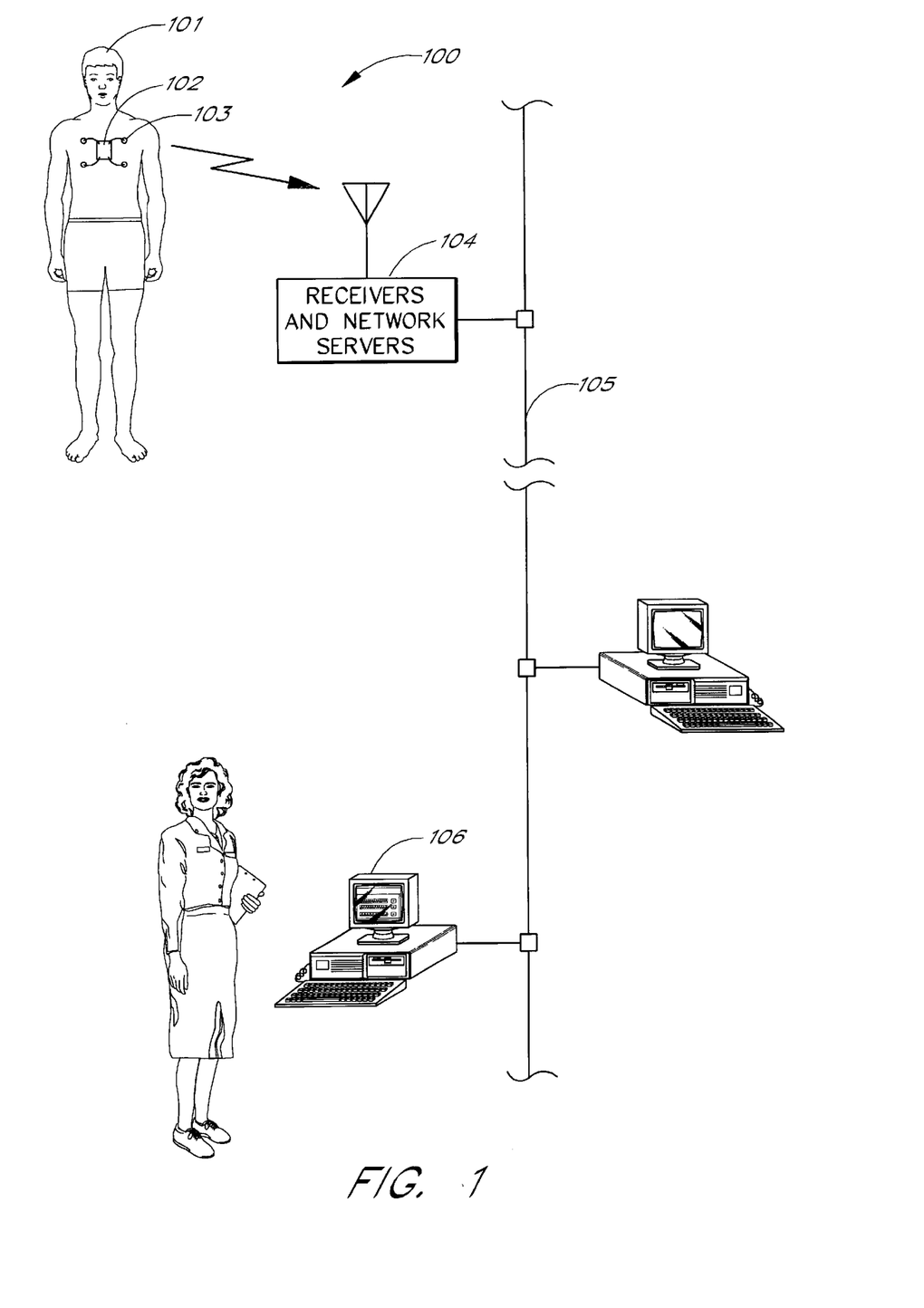
FIG. 1 is an overview of a network-based patient monitoring system.

FIG. 1 is an overview of a network-based patient monitoring system 100. The system 100 comprises a patient 101. A series of sensors 103 (e.g., EKG leads) are attached to the patient 101 to measure various types of physiologic data. The leads 103 are also attached to a medical telemetry device 102. The medical telemetry device 102 transmits the physiological data from the patient 101, to a central station 104. The central station 104 is attached to a network 105. Also attached to the network 105 are a series of workstation computers (workstations) 106. The workstations 106 are typically located at nursing stations throughout the hospital. Nurses and clinicians 107 use the workstations 106 to view the physiologic data collected from the patient 101 and to view hospital patient records.

The workstation 106 typically runs a standard operating system (e.g., Microsoft Windows) and a standard Web browser (e.g., Microsoft's Internet Explorer). In one embodiment, the hospital creates a Web page for each patient and stores the Web page in the hospital database 230 (shown in FIG. 2). The nurse 107 can conveniently view information about the patient 101 contained in the database by using the workstation 106 to open the Web page corresponding the patient 101. If the patient 101 is attached to a telemetry device 102, and the waveform server 104 is receiving physiologic data from the telemetry device 102, then the nurse 107 can view the telemetry data (such as an EKG) using a media player applet loaded by the Web page.

Figure 2:
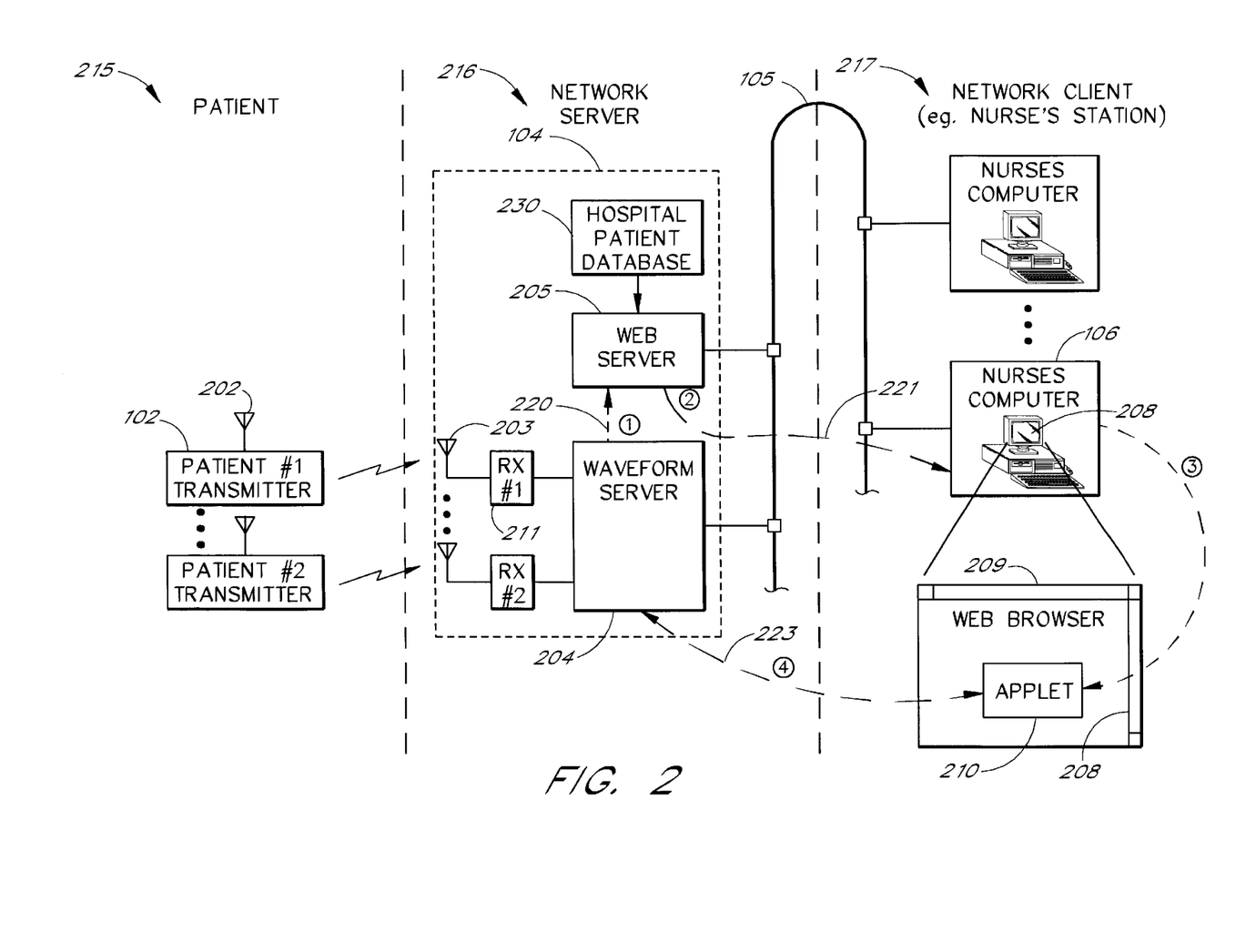
FIG. 2 is a block diagram of a network-based patient monitoring system.

FIG. 2 is a system block diagram of the network-based patient monitoring system 100 wherein the system 100 is described in terms of three major components: a patient component 215, a server component 216, and a client component 217. The patient component 215 comprises one or more patient transmitters 102, each patient transmitter having an antenna 202 for transmitting data to the central station 104. The central server 104 comprises one or more Web servers 205, one or more waveform servers 204 and one or more receivers 211. In input of each receiver 211 is connected to an antenna, and an output of each receiver 211 is connected to at least one of the waveform servers 204. The waveform servers 204 and Web the servers 205 are connected to the network 105. The Web servers 205 are also connected to a hospital database 230. The hospital database 230 contains patient records.

The network client component 217 comprises a series of workstations 106 connected to the network 105. Each workstation 106 runs a World Wide Web (WWW or Web) browser application 208. Each Web browser can open a page that includes one or more media player applets 210. The waveform servers 204 use the network 105 to send a series of messages 220 to the Web servers 205. The Web servers 205 use the network 105 to communicate messages, shown as a path 221, to the workstations 106. The media player applets running on the workstations 106 use the network 105 to send messages over a path 223 directly to the waveform servers 204.

Figure 3:
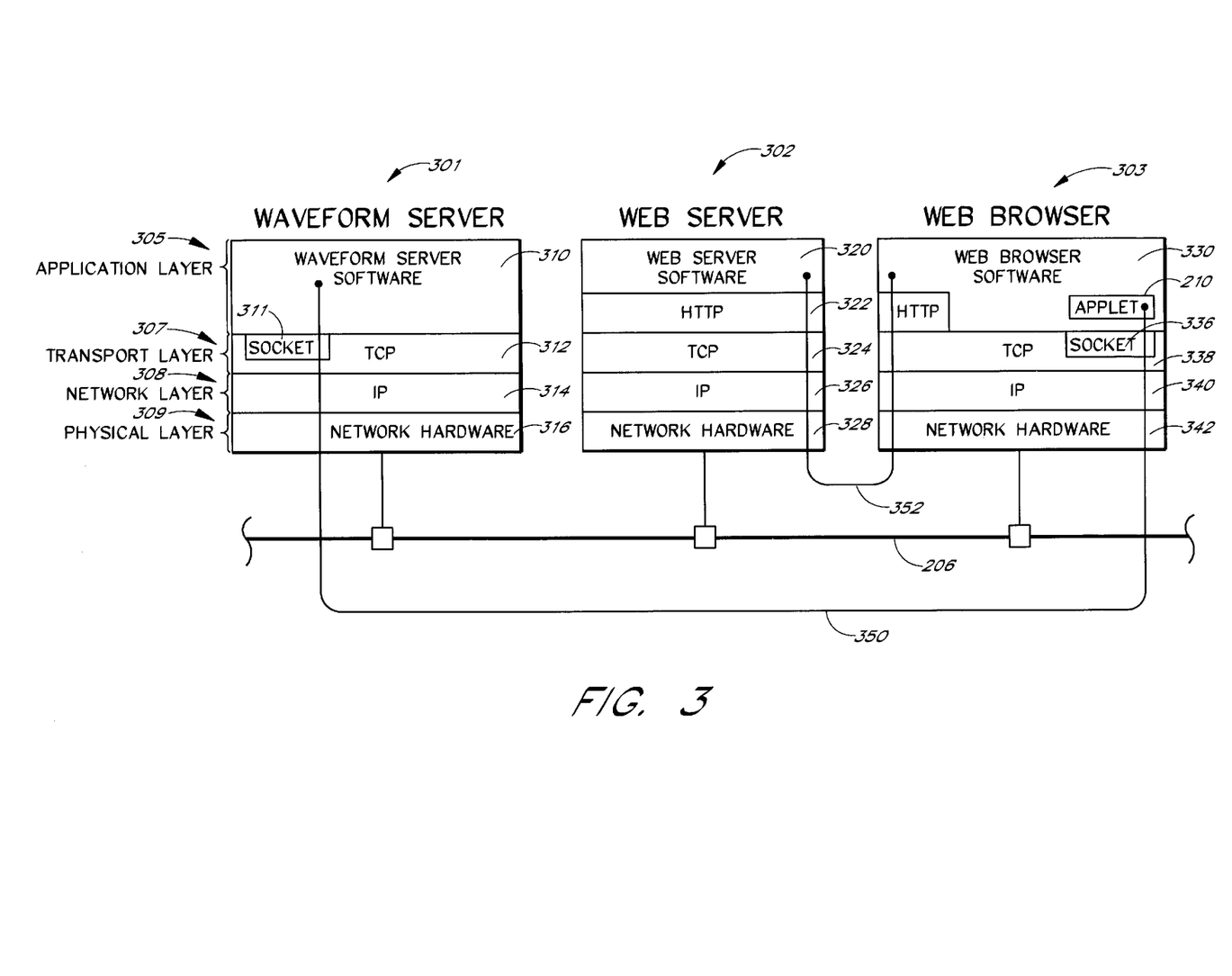
FIG. 3 is a block diagram of the network protocol stacks use to provide communications between the Web server, the waveform server, and the Web browser.

The details of the interprocess communication between the Web servers 205, the waveform servers 204 and the browser application 208 is best understood by examining the layers of software and hardware, know as protocol stacks, shown in FIG. 3. FIG. 3 is a block diagram of the network protocol stacks used to provide communications between the Web servers 205, the waveform servers 204, and the Web browser 208. A waveform stack 301 shows the network protocol stack running on the waveform servers 204, a Web stack 302 shows the network protocol stack running on the Web server 302, and a browser stack 303 shows the network protocol stack running on the workstation 106. Each protocol stack comprises, from top to bottom, an application layer 305, a transport layer 307, a network layer 308, and a physical layer 309.

The physical layer 309 on the waveform stack 301 is a network hardware interface 316. The network layer 308 on the waveform stack 301 is an Internet Protocol (IP) layer 314. The transport layer 307 on the waveform stack 301 is a Transmission Control Protocol (TCP) layer 312. The TCP layer 312 provides a socket interface 311 to a waveform server program 310. The waveform server program 310 runs in the application layer 305 on the waveform stack 301.

The physical layer 309 on the Web stack 302 is a network hardware interface 328. The network layer 308 on the Web stack 302 is an IP layer 326. The transport layer 307 on the Web stack 302 is a TCP layer 324. The application layer 305 on the Web stack 302 is a Web server program 320 overlaying an HTTP layer 322.

The physical layer 309 on the browser stack 303 is a network hardware interface 342. The network layer 308 on the browser stack 303 is an IP layer 340. The transport layer 307 on the browser stack 303 is a TCP layer 338. The TCP layer 338 provides a socket interface 336 to a Web browser program 330. The Web browser program 330 runs in the application layer 305 on the browser stack 303. The Web browser program advantageously provides an HTTP interface 334 and an applet 210. A socket connection 350 connects the socket 311 to the socket 336. The Web server software 320 is connected to the Web browser software 330 by an HTTP connection 352. One skilled in the art will know that any particular layer typically communicates primarily with the layers immediately above or below that layer. The network 105 provides communication between the different stacks. A message sent by the application layer 320 to the application layer 330 propagates through the layers (in order) 322, 324, 326, 328, 342, 340, 338, and 330, as shown by the connection 352. This conceptual model applies even when two applications are running on the same computer (the conceptual model still applies, even though some systems recognize that in such circumstances, the lower layers can be bypassed in order to gain efficiency).

The TCP layers 312, 324, and 338, and the IP layers 314, 326, and 340, (more commonly known as TCP/IP) work together to provide the necessary data transmission and error correction functions needed to transfer of data from one network linked computer to another network linked computer.

The IP portion of TCP/IP is a connectionless protocol that describes how an Internet connected computer should break data down into packets for transmission across the network, and how those packets should be addressed so that they arrive at their destination. A connectionless protocol is a protocol that enables the transmission of data from one computer to another, even though no effort is made to determine whether the receiving computer is on-line or able to receive the information. All packet switching networks use some form of connectionless protocol. IP is the lowest level of the TCP/IP structure and it is concerned only with breaking data down into packets for transmission, and reassembling the packets after they have been received.

TCP is a connection-oriented protocol that establishes a procedure by which two computers on the network can establish a connection that lasts until the two computers have successfully exchanged data. This is accomplished by means of handshaking in which the two computers exchange messages. Handshaking is similar to registered mail. In a handshaking transaction: the first computer sends a "ready" message indicating that it is ready to accept data; when the second computer receives the ready message, it responds by sending data to the first computer; finally, when the first computer receives the data, it sends a "data received" message back to the second computer. The handshaking ensures that the data was sent and properly received. When an error does occur, both computers will be aware of the error and arrange to re-send the data.

Software programs running in the application layer 305 generally access the services of TCP through the use of a general purpose interprocess communication (IPC) mechanism known a socket (a socket connection). The socket connection is a logical entity through which a first process (or program) communicates with a second process. Sockets can use any communication protocol, but generally TCP/IP is preferred. The first and second processes may be running on the same computer, or they may be running on separate computers (when the two computers are connected by a network). Each socket is associated with a socket identification (ID) comprising an IP address and a port number. The IP address identifies the network address of the second computer. The port number identifies a particular application running on the second computer (the computer identified by the IP address). Some well-known software applications have standardized port numbers, known as "well known ports." Thus, for example, standard Internet applications such as Telnet, File Transfer Protocol (FTP) and Web browsers all correspond to specific ports.

Since sockets are generic, different parts of an application program can execute on several different machines simultaneously, and an application can open more than one socket at a time. In the present invention, the waveform server usually runs on a first computer, the Web (HTTP)

server runs on a second computer, and the waveform viewer (the applet 210) runs on a third computer. A process or function associated with a socket is known as a socket client. The socket client is said to "own" the socket; that is, it can make use of the socket to request and receive information and network services. Raw sockets are used for communications by low-level protocols, and are usually available only to privileged program. Stream sockets, are higher-level mechanisms that provide reliable connections that guarantee delivery of the data.

The Web browser 209 and the web server s communicate using a high-level protocol known as HTTP. HTTP is an application layer protocol for distributed, collaborative, hypernedia information systems. It is a generic, object-oriented protocol which can be used for many tasks, including file transfer, news, electronic mail, etc. HTTP uses the TCP protocol for data transport. However, the effects of HTTP's inefficient use of TCP on the Internet have resulted in major problems caused by congestion and unnecessary overhead.

Unfortunately, many of the solutions proposed for improving HTTP performance are largely ineffective with regards to real-time telemetry data. For example, caching of telemetry data is ineffective because caching presupposes that the data stored on the server has not changed since the last access. Telemetry data is continuously changing and typically does not benefit from being cached.

The current trend in the art is to improve the performance of Web pages that use HTTP by making changes to HTTP itself. The present invention uses an entirely different solution not suggested by the current efforts to improve HTTP. The present invention avoids the inefficiencies of HTTP by using HTTP only for the purposes for which it is suited, such as formatting textual information, downloading slowly changing data (e.g., patient records from the hospital database 230), and running small applications (e.g., the applet 210). The present invention uses other standard methods, such as a direct socket connection, to provide rapid, near real-time waveform data to the workstation 106. In the present invention, a workstation 106, running a Web browser stack 303, uses HTTP to open a Web page corresponding to a patient 101. Messages are passed between the Web browser 330 and the Web server 332 using the relatively inefficient HTTP protocol. The Web browser 303 loads a Web page 209, which displays relatively static (or quasi-static) fields such as patient name, room, etc. The Web page also displays a window for showing real-time patient physiologic information, such as an EKG. The Web page loads an applet 210 (a small program run from within the Web browser) which begins to run once the Web page 209 is loaded. In one embodiment, the applet 210 is written in the JAVA programming language.

Once the applet 210 begins to run, the applet 210 opens a socket connection 336. The socket 336 connects to a socket 311 on the waveform server via a socket connection 350. Once the socket connection 350 established, the applet 210 is able to send requests, and receive data from, the waveform server 310.

Figure 4:
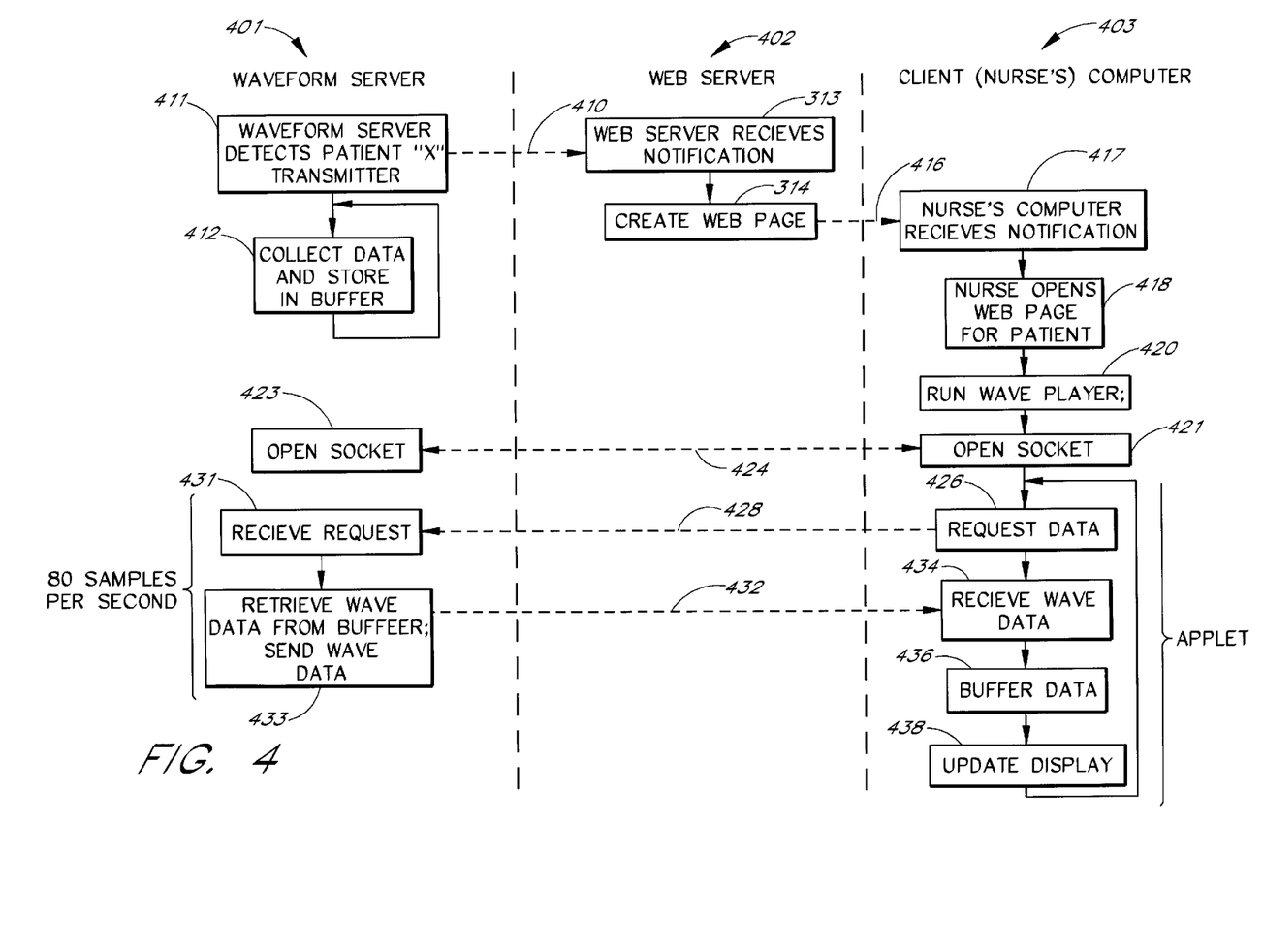
FIG. 4 is a messaging diagram of the messages passed between the Web serve, waveform server, and workstations (workstations) in a network based patient monitoring system.

FIG. 4 is a time-sequence diagram of the messages passed between the Web servers 205, the waveform servers 204 and the workstation 106 (the Web browser 330 and the applet 210 both run on the workstation 106). One skilled in the art will understand that a time-sequence diagram refers to a technique for graphically representing events occurring in a software system. In such a diagram, time is represented on a vertical axis, with the oldest events at the top and the most recent events at the bottom. The information presented horizontally shows messages traveling from one computer to another.

FIG. 4 shows a column 401 corresponding to operations performed by the waveform servers 204, a column 402 corresponding to operations performed by the Web servers 205, and a column 403 corresponding to operations performed by the workstations 106. In a process block 411, the waveform servers 204 detect transmissions from a patient transmitter 102. Upon detecting the transmissions, the waveform servers 204 send a notification message 410 to the Web servers 205 and then transitions to a process block 412. In the process block 412 the waveform servers 204 collect and buffer data from the patient transmitter 102. A thread in the waveform servers 204 loops in the process block 412 until the data collection and buffering operation is terminated by some external event (e.g., the patient transmitter 102 is turned off).

The Web server receives the notification message 410 in a process block 413. Upon receipt of the notification 410, the Web server transitions to a process block 414 where it creates a new Web page corresponding to the patient 101. Upon creation of the new Web page, the Web servers 205 send a notification message 416 to the workstation 106. The workstation 106 receives the notification message 416 in a process block 417. In the process block 417, the workstation 106 notifies the user (e.g., the Nurse) that the new Web page, corresponding to a new patient 102, is available. The workstation 106 then transitions to a process block 418 where the user opens the Web page to view the data corresponding to the patient 101. After opening the Web page in the process block 418, the workstation 106 transitions to a process block 420 where the workstation runs a media player applet 210 attached to the Web page. The media player applet 210 opens a socket connection 350 to the waveform servers 204 and sends a notification message 424 to the waveform server. The waveform servers 204 receive the notification message 424 in a process block 423 and sends a return notification message 424 to the applet 210.

Upon receipt of the return notification message 424, the applet 210 transitions to a process block 426. In the process block 426, the applet sends a data request message 428 to the waveform servers 204. The waveform servers 204 receive the data request 428 in a process block 431. Upon receipt of the message 428 in the process block 431, the waveform servers 204 retrieve data from the data buffer and transitions to a process block 433 to send the data. In the process block 433, the waveform servers 204 send the patient data to the workstation 106 using a message 432. The workstation 106 receives the data message 432 in a process block 434. Upon receipt of the data in the process block 434, the workstation 106 advances to a process block 436 where it stores the data in a buffer. The workstation 106 then advances to a process block 438 where it retrieves data from the buffer and updates a display showing patient data. After updating the display, the workstation 106 jumps back to the process block 426 to retrieve more data. The workstation 106 continues the loop of requesting data in the process block 426, receiving data in the process block 434, buffering the data in the process block 436, and displaying the data in the process block 438 until either the patient transmitter goes offline (in which case there is no more data to display), or the nurse or user of the workstation 106 closes the applet 210.

The socket connection 350 provides a fast, low overhead, method for the media player applet 210 to retrieve the EKG data from the waveform server. In a preferred embodiment, the media player 210 reads 80 samples/second in a single 80 byte transfer (8 bit samples) once per second. The media player 210 buffers 4 to 5 seconds of data in a circular ring buffer.

Figure 5:
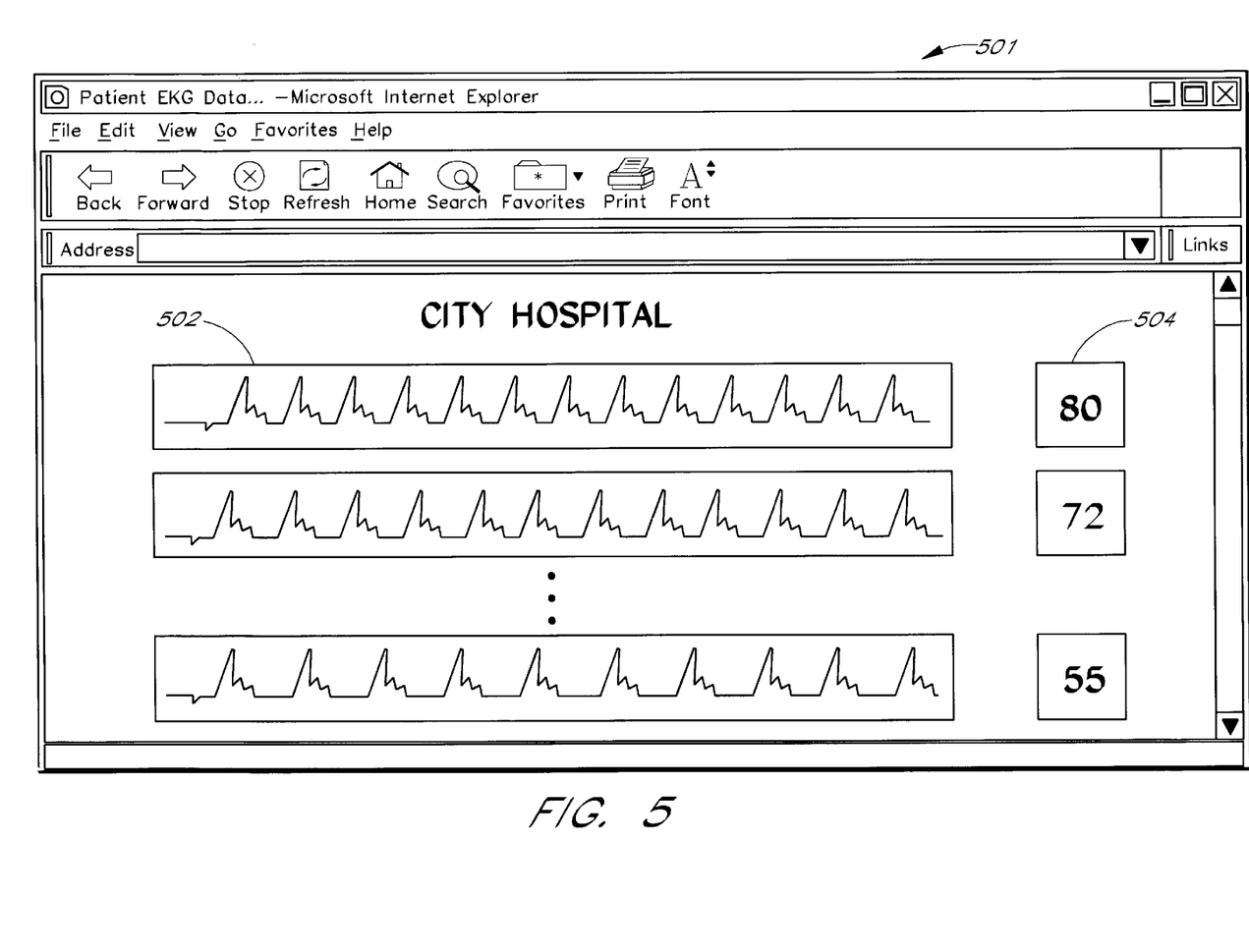
FIG. 5 is an exemplary screen display of a patient's EKG and heart rate.

FIG. 5 is an exemplary screen display of a patient EKG and heart rate. FIG. 5 shows the Web page 208 having a series of displays as exemplified by the EKG display 502 showing a plot of EKG data in a number display 504 showing patient heart rate corresponding to the EKG 502. One skilled in the art will recognize that EKG data can be shown either by a scrolling waveform that moves along the screen display, or by a moving bar where the waveform is essentially stationary and the bar moves across the screen.

Other Embodiments

While the present invention has been particularly shown and described with reference to preferred embodiments thereof, it will be understood by those skilled in the art that various changes in form and detail may be made therein without departing from the spirit, scope and teaching of the invention. Accordingly, the embodiments herein disclosed are to be considered merely as illustrative and limited in scope only as specified in the appended claims.

What is claimed is:

1. A patient monitoring system for providing patient data to one or more workstations connected to a computer network, said system comprising:
   one or more sensors attached to said patient, said sensors configured to measure physiologic data from said patient;
   a patient monitoring device attached to said one or more sensors, said patient monitoring device configured to gather said physiologic data and use a communication system to communicate said physiologic data to a central data monitoring device;
   one or more data servers connected to said computer network, said data servers configured to supply data to said workstations using a first protocol; and
   one or more waveform servers connected to said central data monitoring device, said waveform servers receiving said physiologic information from said central data monitoring device, said waveform servers connected to said computer network, said waveform servers configured to supply said physiologic data to said workstations using a second protocol.

2. The patient monitoring system of claim 1, wherein said communication system comprises a wireless link between said patient monitoring device and said central data monitoring device.

3. The patient monitoring system of claim 1, wherein said first protocol is a low level network protocol.

4. The patient monitoring system of claim 3, wherein said first protocol is TCP/IP.

5. The patient monitoring system of claim 3, wherein said second protocol is a high level protocol.

6. The patient monitoring system of claim 5, wherein said second protocol uses said first protocol.

7. The patient monitoring system of claim 6, wherein said first protocol is TCP/IP and said second protocol is HTTP.

8. The patient monitoring system of claim 1, wherein said second protocol is a high level protocol.

9. The patient monitoring system of claim 8, wherein said high level protocol is an application level protocol.

10. The patient monitoring system of claim 1, further comprising a first software program stored within a memory in said workstations, said software configured to communicate with said data server using said first protocol.

11. The patient monitoring system of claim 10, wherein said first software program is configured to run a second software program substantially contemporaneously with said first software program.

12. The patient monitoring system of claim 11, wherein said second software program is configured to communicate with at least one of said waveform servers using said first protocol.

13. The patient monitoring system of claim 11, wherein said second software program is configured to obtain said physiologic data from at least one of said waveform servers by communicating with said at least one of said waveform servers using said first protocol.

14. The patient monitoring system of claim 13, wherein said second software program is configured to obtain said physiologic data from said at least one of said waveform servers in data packets with varying latency periods, and wherein said second software program is configured to display said physiologic data on a display device such that it appears to a person observing said display device that physiologic data is being received as a stream of data with uniform latency periods.

* * * * *